US010827802B2

(12) United States Patent
Beers et al.

(10) Patent No.: US 10,827,802 B2
(45) Date of Patent: **\*Nov. 10, 2020**

(54) INPUT ASSEMBLY FOR AN ARTICLE OF MANUFACTURE

(71) Applicant: NIKE, Inc., Beaverton, OR (US)

(72) Inventors: Tiffany A. Beers, Portland, OR (US); Andrew A. Owings, Portland, OR (US); Steven H. Walker, Camas, WA (US)

(73) Assignee: NIKE, Inc., Beaverton, OR (US)

( * ) Notice: Subject to any disclaimer, the term of this patent is extended or adjusted under 35 U.S.C. 154(b) by 107 days.

This patent is subject to a terminal disclaimer.

(21) Appl. No.: 16/113,087

(22) Filed: Aug. 27, 2018

(65) Prior Publication Data

US 2019/0090588 A1 Mar. 28, 2019

Related U.S. Application Data

(63) Continuation of application No. 15/070,395, filed on Mar. 15, 2016, now Pat. No. 10,104,937.

(51) Int. Cl.
*A43C 11/00* (2006.01)
*A43B 3/00* (2006.01)
(Continued)

(52) U.S. Cl.
CPC ............ *A43C 11/00* (2013.01); *A43B 3/0005* (2013.01); *A43B 3/26* (2013.01); *A43C 11/16* (2013.01);
(Continued)

(58) Field of Classification Search
CPC ......... A43B 3/0005; A43B 3/26; A43C 11/00; A43C 11/16
See application file for complete search history.

(56) References Cited

U.S. PATENT DOCUMENTS 5,533,911 A * 7/1996 Elam .................. H01R 13/5833
439/459
6,427,361 B1 * 8/2002 Chou ..................... A43B 11/00
36/138
(Continued)

FOREIGN PATENT DOCUMENTS

CN 202455703 9/2012
CN 104822284 8/2015
(Continued)

OTHER PUBLICATIONS

"U.S. Appl. No. 15/070,395, PTO Response to Rule 312 Communication dated Sep. 25, 2018", 2 pgs.
(Continued)

*Primary Examiner* — Timothy J Thompson
*Assistant Examiner* — Rhadames Alonzo Miller
(74) *Attorney, Agent, or Firm* — Schwegman Lundberg & Woessner, P.A.

(57) ABSTRACT

An article of footwear, an article of apparel or protective gear can include a tensioning apparatus for tightening, for example, laces, cables or strings or other devices that secure the article to a wearer. The tensioning apparatus receives signals from an input assembly that is in communication with the tensioning apparatus. The input assembly may include pairs of wires that have twisted loops or other curvilinear segments that allow the input assembly to accommodate to different actions by the wearer of the footwear. The input assembly may also include a flexible epoxy cover that protects the connections between the wires and a printed circuit board that includes input devices.

20 Claims, 7 Drawing Sheets

(51) Int. Cl.
    *A43B 3/26*       (2006.01)
    *A43C 11/16*     (2006.01)
    *A63B 71/08*     (2006.01)
    *A61F 5/01*       (2006.01)
    *A63B 71/10*     (2006.01)
    *A63B 71/12*     (2006.01)

(52) U.S. Cl.
    CPC ............... *A61F 5/01* (2013.01); *A63B 71/08* (2013.01); *A63B 71/10* (2013.01); *A63B 71/12* (2013.01); *A63B 2071/125* (2013.01)

(56) References Cited

U.S. PATENT DOCUMENTS

| | | | | |
|---|---|---|---|---|
| 6,723,923 | B2* | 4/2004 | Tsukamoto | B60R 16/0215 174/68.1 |
| 6,922,917 | B2* | 8/2005 | Kerns | A43B 5/14 36/50.1 |
| 7,075,011 | B1 | 7/2006 | Kogure et al. | |
| 7,339,112 | B2 | 3/2008 | Itou et al. | |
| 7,752,774 | B2* | 7/2010 | Ussher | A43B 3/0005 36/100 |
| 7,822,310 | B2 | 10/2010 | Castonguay et al. | |
| 7,889,961 | B2 | 2/2011 | Cote et al. | |
| 8,141,277 | B2* | 3/2012 | Robinson | A43B 3/0005 36/137 |
| 8,387,282 | B2 | 3/2013 | Baker et al. | |
| 9,241,539 | B1* | 1/2016 | Keswin | A43C 19/00 |
| 10,104,937 | B2 | 10/2018 | Beers et al. | |
| 2002/0100188 | A1* | 8/2002 | Jacques | A43B 3/0005 36/50.1 |
| 2003/0204938 | A1* | 11/2003 | Hammerslag | A43B 5/16 24/68 SK |
| 2004/0130848 | A1 | 7/2004 | Lee et al. | |
| 2008/0301919 | A1* | 12/2008 | Ussher | A43B 3/0005 24/712.7 |
| 2008/0307673 | A1* | 12/2008 | Johnson | A43B 11/00 36/50.1 |
| 2010/0258329 | A1* | 10/2010 | Engelbach | G01D 11/245 174/50 |
| 2011/0175744 | A1* | 7/2011 | Englert | A43B 1/0054 340/665 |
| 2013/0086816 | A1* | 4/2013 | Johnson | A43C 11/00 36/83 |
| 2013/0104429 | A1* | 5/2013 | Torres | A43B 3/0005 36/136 |
| 2013/0122342 | A1 | 5/2013 | Rapisarda | |
| 2014/0070042 | A1* | 3/2014 | Beers | A61F 5/028 242/413 |
| 2014/0082963 | A1* | 3/2014 | Beers | A43C 11/00 36/83 |
| 2015/0250268 | A1* | 9/2015 | Alt | A43C 11/20 24/68 SK |
| 2015/0296922 | A1* | 10/2015 | Rushbrook | A43B 23/16 36/68 |
| 2017/0265571 | A1 | 9/2017 | Beers et al. | |
| 2017/0265582 | A1* | 9/2017 | Walker | G01L 1/12 |
| 2017/0265587 | A1* | 9/2017 | Walker | A43C 11/008 |
| 2018/0073168 | A1* | 3/2018 | Gladish | H01R 13/035 |
| 2018/0084867 | A1* | 3/2018 | Feinstein | A43C 11/002 |
| 2018/0084868 | A1* | 3/2018 | Feinstein | A43B 23/0215 |

FOREIGN PATENT DOCUMENTS

| | | |
|---|---|---|
| CN | 109152444 | 1/2019 |
| CN | 111513427 A | 8/2020 |
| WO | WO-2017160998 A1 | 9/2017 |

OTHER PUBLICATIONS

"International Application Serial No. PCT/US2017/022531, International Preliminary Report on Patentability dated Sep. 27, 2018", 7 pgs.

"U.S. Appl. No. 15/070,395, Notice of Allowance dated May 22, 2018", 13 pgs.

"International Application Serial No. PCT/US2017/022531, International Search Report dated Jun. 26, 2017", 3 pgs.

"International Application Serial No. PCT/US2017/022531, Written Opinion dated Jun. 26, 2017", 6 pgs.

"Chinese Application Serial No. 201780029314.6, Voluntary Amendment filed Feb. 22, 2019", w English claims, 17 pgs.

"European Application Serial No. 17767441.3, Response filed Apr. 26, 2019 to Communication Pursuant to Rules 161 and 162 dated Oct. 31, 2018", 21 pgs.

"Chinese Application Serial No. 201780029314.6, Office Action dated Apr. 26, 2019", w English Translation, 9 pgs.

"Eurasian Application Serial No. 17767441.3, Extended European Search Report dated Oct. 15, 2019", 5 pgs.

"Chinese Application Serial No. 201780029314.6, Response filed Nov. 4, 2019 to Office Action dated Apr. 26, 2019", w English Claims, 14 pgs.

U.S. Appl. No. 15/070,395, filed Mar. 15, 2016, Input Assembly For an Article of Manufacture.

"Eurasian Application Serial No. 17767441.3, Response filed Apr. 20, 2020 to Extended European Search Report dated Oct. 15, 2019", 32 pgs.

\* cited by examiner

INPUT ASSEMBLY FOR AN ARTICLE OF MANUFACTURE

BACKGROUND

The present embodiments relate generally to articles of manufacture such as articles of footwear, articles of apparel and protective gear.

Articles of footwear generally include two primary elements: an upper and a sole structure. The upper is often formed from a plurality of material elements (e.g., textiles, polymer sheet layers, foam layers, leather, and synthetic leather) that are stitched or adhesively bonded together to form a void on the interior of the footwear for comfortably and securely receiving a foot. More particularly, the upper forms a structure that extends over instep and toe areas of the foot, along medial and lateral sides of the foot, and around a heel area of the foot. The upper may also incorporate a closure system to adjust the fit of the footwear, as well as permitting entry and removal of the foot from the void within the upper. Likewise, some articles of apparel, such as pants, shorts, hoodies, jogging bras, and certain protective gear such knee braces, shoulder pads, helmets and knee pads may include various kinds of closure systems for adjusting the fit of the apparel or protective gear.

SUMMARY

In one aspect, the present disclosure is directed to an article of footwear, comprising an upper and a sole structure, and a tensioning apparatus. The tensioning apparatus is controlled according to signals received from an input device. The input device is electrically connected to the tensioning apparatus by an input assembly.

In one embodiment, the input assembly has a first pair of conductors that have a proximal end and a distal end. The first pair of conductors has a first conductor and a second conductor, each of which has a proximal end and a distal end. The input assembly also has a second pair of conductors that have a proximal end and a distal end. The second pair of conductors has a third conductor and a fourth conductor, each of which has a proximal end and a distal end. The input assembly also includes a printed circuit board that has a first connection point, a second connection point, a third connection point and a fourth connection point. The first conductor is connected at its distal end to the first connection point, the second conductor is connected at its distal end to the second connection point, the third conductor is connected at its distal end to the third connection point and the fourth conductor is connected at its distal end to the fourth connection point. The first pair of conductors form a first twisted loop between the distal end of the first pair of conductors and the proximal end of the first pair of conductors. The second pair of conductors form a second twisted loop between the distal end of the second pair of conductors and the proximal end of the second pair of conductors, such that the first twisted loop and the second twisted loop form opposed twisted loops. The first twisted loop has a first diameter and the second twisted loop has a second diameter. The first twisted loop includes a first inner retaining member slidably holding both the first conductor and the second conductor. The second twisted loop includes a second inner retaining member slidably holding both the third conductor and the fourth conductor.

In another embodiment, the input assembly has a first pair of conductors that has a proximal end and a distal end. The first pair of conductors has a first conductor that has a proximal end and a distal end, and a second conductor that has a proximal end and a distal end. The input assembly also has a second pair of conductors that has a proximal end and a distal end. The second pair of conductors has a third conductor that has a proximal end and a distal end and a fourth conductor that has a proximal end and a distal end. The input assembly also has a printed circuit board that has a first connection point, a second connection point, a third connection point and a fourth connection point. The first conductor is connected at its distal end to the first connection point, the second conductor is connected at its distal end to the second connection point, the third conductor is connected at its distal end to the third connection point and the fourth conductor is connected at its distal end to the fourth connection point. The first pair of conductors forms a first curved segment that has a first radius of curvature, such that when the distance between the distal end of the first pair of conductors and the proximal end of the first pair of conductors increases, the first radius of curvature decreases. The second pair of conductors forms a second curved segment that has a second radius of curvature, such that when the distance between the distal end of the second pair of conductors and the proximal end of the second pair of conductors increases, the second radius of curvature decreases. The first curved segment includes a first inner retaining member slidably holding both the first conductor and the second conductor. The second curved segment includes a second inner retaining member slidably holding both the third conductor and the fourth conductor.

In another embodiment, the input assembly includes a printed circuit board that has a first connection point, a second connection point, a third connection point and a fourth connection point. The input assembly has a first pair of conductors that has a proximal end and a distal end, and a second pair of conductors that has a proximal end and a distal end. The first pair of conductors has a first conductor and a second conductor, and the second pair of conductors has a third conductor and a fourth conductor. The first conductor has a distal end and a proximal end, the second conductor has a distal end and a proximal end, the third conductor has a distal end and a proximal end and the fourth conductor has a distal end and a proximal end. The first conductor is connected at its distal end to the first connection point, the second conductor is connected at its distal end to the second connection point, the third conductor is connected at its distal end to the third connection point and the fourth conductor is connected at its distal end to the fourth connection point. The first pair of conductors form a first loop and the second pair of conductors form a second loop such that the first loop and the second loop lie in substantially the same plane. The first loop includes a first length of the first conductor within the first loop and the second loop includes a third length of the third conductor within the second loop. When the distance between the proximal end of the first pair of conductors and the distal end of the first pair of conductors decreases, the first length of the first conductor within the first loop increases and the third length of the third conductor within the second loop increases. The first loop includes a first inner retaining member slidably holding both the first conductor and the second conductor together, and the second loop includes a second inner retaining member slidably holding both the third conductor and the fourth conductor together.

Other systems, methods, features, and advantages of the embodiments will be, or will become, apparent to one of ordinary skill in the art upon examination of the following figures and detailed description. It is intended that all such additional systems, methods, features, and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION

The following discussion and accompanying figures disclose embodiments of an input assembly used in a tensioning apparatus of an article of footwear. Concepts associated with the footwear disclosed herein may be applied to a variety of athletic footwear types, including running shoes, basketball shoes, soccer shoes, baseball shoes, football shoes, and golf shoes, for example. The input assembly may also be used with articles of apparel such as pants, shirts, blouses, shorts, jogging bras, sweatpants, sweatshirts, headgear and hoodies, as well as with protective gear such as knee braces, knee pads, elbow pads and helmets. Accordingly, the concepts disclosed herein apply to a wide variety of footwear types, a wide variety of articles of apparel and a wide variety of protective gear.

Exemplary articles of footwear that incorporate a tensioning apparatus are disclosed, for example, in Beers et al., now Patent Application Publication Number 20160345655, published on Dec. 1, 2016, U.S. patent application Ser. No. 14/724,007, filed May 28, 2015, entitled "A Control Device For An Article Of Footwear," and Baker et al., U.S. Pat. No. 8,387,282, issued on Mar. 3, 2013 and entitled "Cable Tightening System For An Article Of Footwear," which are both incorporated by reference herein in their entireties.

To assist and clarify the subsequent description of various embodiments, various terms are defined herein. Unless otherwise indicated, the following definitions apply throughout this specification (including the claims). For consistency and convenience, directional adjectives are employed throughout this detailed description corresponding to the illustrated embodiments.

The term "longitudinal," as used throughout this detailed description and in the claims, refers to a direction extending a length of a component. For example, a longitudinal direction of an article of footwear extends between a forefoot region and a heel region of the article of footwear. The term "forward" is used to refer to the general direction in which the toes of a foot point, and the term "rearward" is used to refer to the opposite direction, i.e., the direction in which the heel of the foot is facing.

The term "lateral direction," as used throughout this detailed description and in the claims, refers to a side-to-side direction extending a width of a component. In other words, the lateral direction may extend between a medial side and a lateral side of an article of footwear, with the lateral side of the article of footwear being the surface that faces away from the other foot, and the medial side being the surface that faces toward the other foot.

The term "side," as used in this specification and in the claims, refers to any portion of a component facing generally in a lateral, medial, forward, or rearward direction, as opposed to an upward or downward direction.

The term "vertical," as used throughout this detailed description and in the claims, refers to a direction generally perpendicular to both the lateral and longitudinal directions. For example, in cases where a sole is planted flat on a ground surface, the vertical direction may extend from the ground surface upward. It will be understood that each of these directional adjectives may be applied to individual components of a sole. The term "upward" refers to the vertical direction heading away from a ground surface, while the term "downward" refers to the vertical direction heading towards the ground surface. Similarly, the terms "top," "upper," and other similar terms refer to the portion of an object substantially furthest from the ground in a vertical direction, and the terms "bottom," "lower," and other similar terms refer to the portion of an object substantially closest to the ground in a vertical direction.

The "interior" of a shoe refers to space that is occupied by a wearer's foot when the shoe is worn. The "inner side" of a panel or other shoe element refers to the face of that panel or element that is (or will be) oriented toward the shoe interior in a completed shoe. The "outer side" or "exterior" of an element refers to the face of that element that is (or will be) oriented away from the shoe interior in the completed shoe. In some cases, the inner side of an element may have other elements between that inner side and the interior in the completed shoe. Similarly, an outer side of an element may have other elements between that outer side and the space external to the completed shoe. Further, the terms "inward" and "inwardly" shall refer to the direction toward the interior of the shoe, and the terms "outward" and "outwardly" shall refer to the direction toward the exterior of the shoe.

For purposes of this disclosure, the foregoing directional terms, when used in reference to an article of footwear, shall refer to the article of footwear when sitting in an upright position, with the sole facing towards the ground, that is, as it would be positioned when worn by a wearer standing on a substantially level surface.

Figure 1:
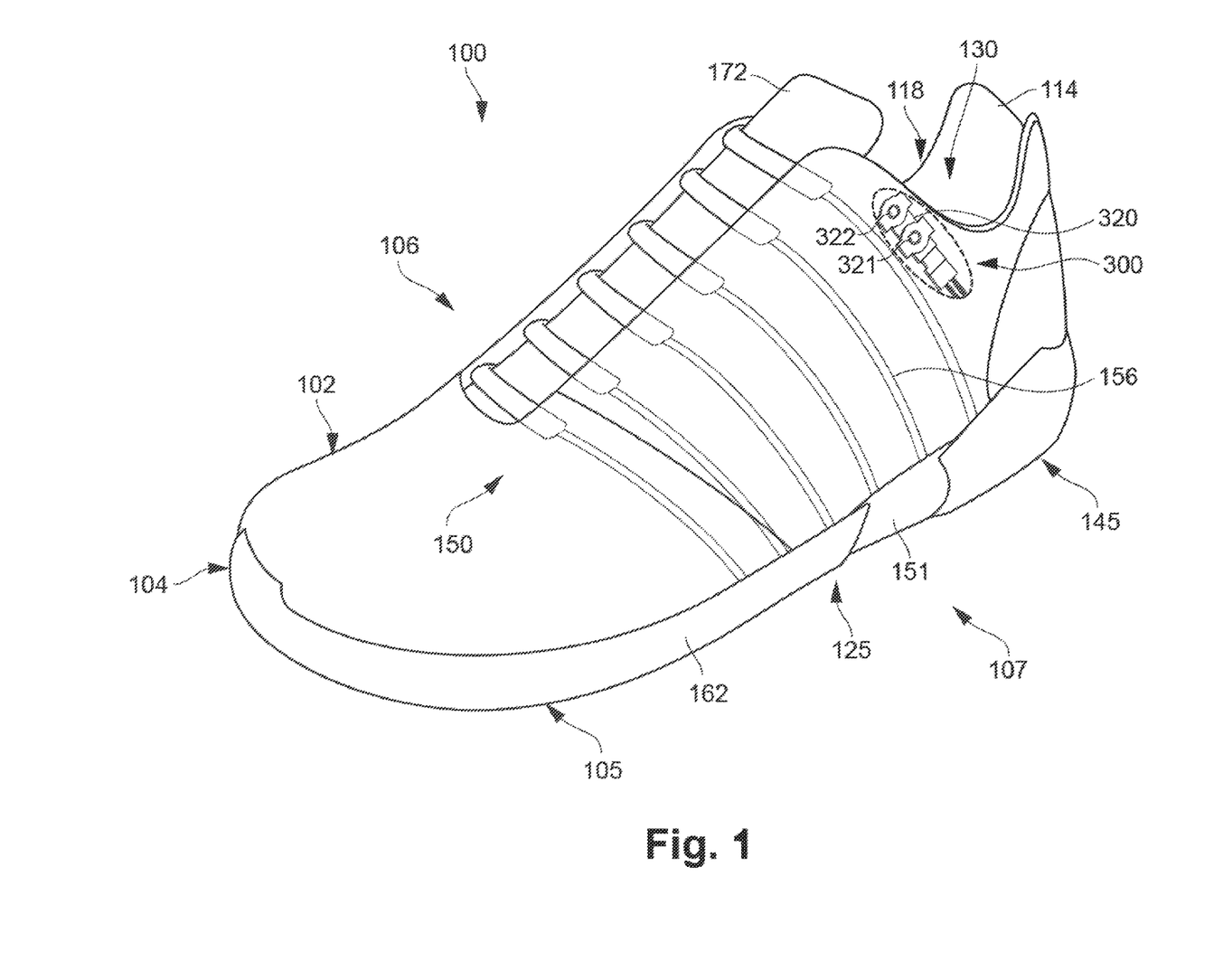
FIG. 1 is an isometric schematic diagram of an embodiment of an article of footwear.
Figure 2:
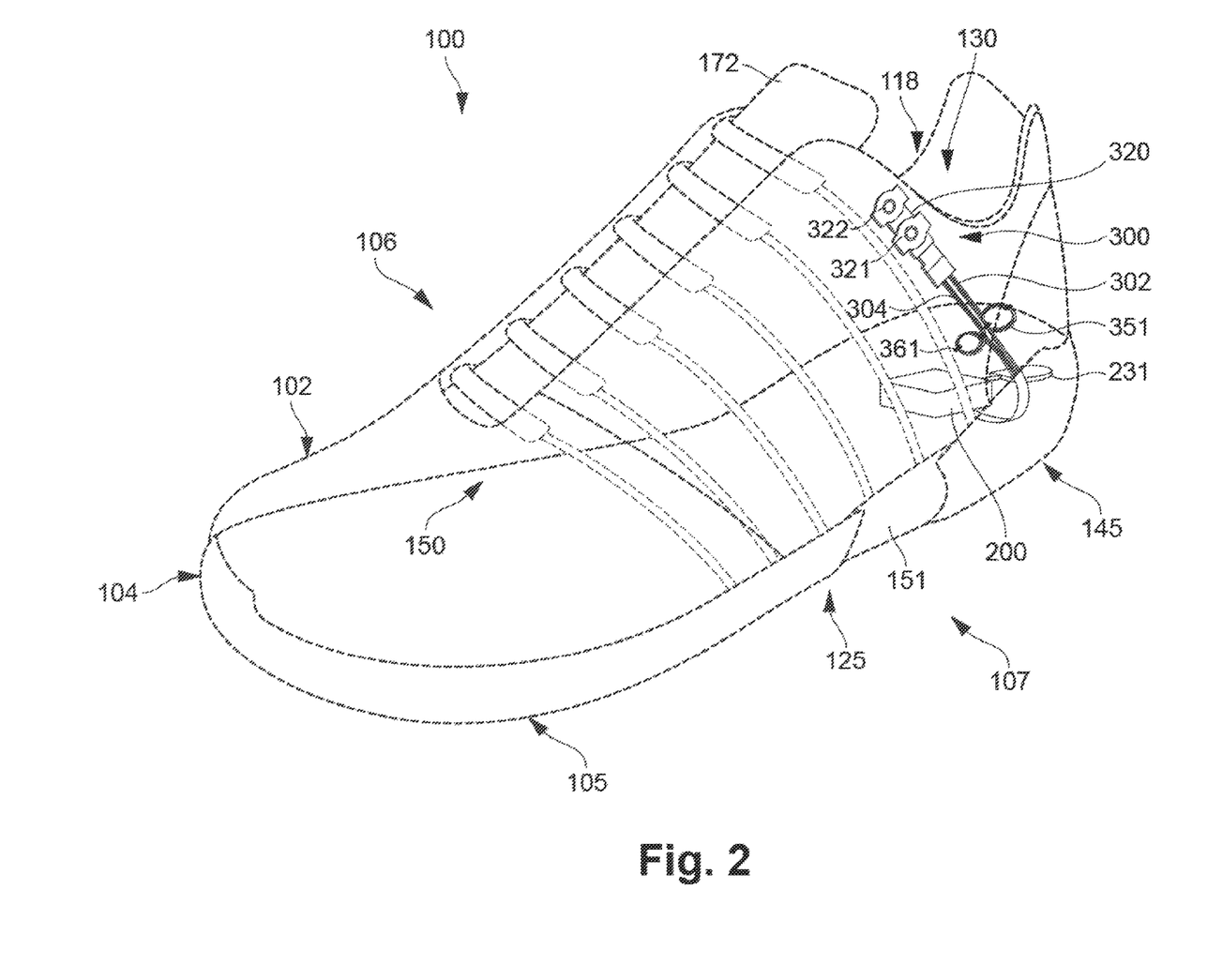
FIG. 2 is a schematic diagram of the embodiment of FIG. 1, illustrating an embodiment of the input assembly.

FIG. 1 and FIG. 2 illustrate an embodiment of article of footwear 100 that is configured with an input assembly 300 and a tensioning apparatus 200 (shown schematically in FIG. 2). In the current embodiment, article of article of footwear 100 is shown in the form of an athletic shoe. Tensioning apparatus 200 and input assembly 300 may also be used with any other kind of footwear including, but not limited to: hiking boots, soccer shoes, football shoes, sneakers, running shoes, cross-training shoes, rugby shoes, walking shoes, basketball shoes, baseball shoes as well as other kinds of shoes. As pointed out above, embodiments of a tensioning apparatus described herein may not be limited to footwear—in other embodiments a tensioning apparatus and/or components associated with a tensioning apparatus could be used with various kinds of apparel, including clothing such as shirts, shorts, pants, hoodies, other sportswear, other sporting equipment and other kinds of apparel. In still other embodiments, a tensioning apparatus may be used with braces, such as orthopedic braces or with protective gear such as helmets, knee pads, shoulder pads and elbow pads.

As noted above, for consistency and convenience, directional adjectives are employed throughout this detailed description. Article of footwear 100 may be divided into three general regions along the longitudinal direction: a forefoot region 105, a midfoot region 125, and a heel region 145. Forefoot region 105 generally includes portions of article of footwear 100 corresponding with the toes and the joints connecting the metatarsals with the phalanges. Midfoot region 125 generally includes portions of article of footwear 100 corresponding with an arch area of the foot. Heel region 145 generally corresponds with rear portions of the foot, including the calcaneus bone. Forefoot region 105, midfoot region 125, and heel region 145 are not intended to demarcate precise areas of article of footwear 100. Rather, forefoot region 105, midfoot region 125, and heel region 145 are intended to represent general relative areas of article of footwear 100 to aid in the following discussion.

Article of footwear 100 may include upper 102 and sole structure 104. Generally, upper 102 may be any type of upper. In particular, upper 102 may have any design, shape, size and/or color. For example, in embodiments where article of footwear 100 is a basketball shoe, upper 102 could be a high top upper that is shaped to provide high support on an ankle. In embodiments where article of footwear 100 is a running shoe, upper 102 could be a low top upper.

Furthermore, as shown in FIG. 1, article of footwear 100 may include a tongue 172, which may be provided near or along throat opening 130. However, in other embodiments, tongue 172 may be disposed along other portions of an article of footwear, or an article of footwear may not include a tongue. Throat opening 130 allows a wearer to insert his or her foot into the interior void 118 of article of footwear 100. Lacing system 150, which is part of tensioning system 200, allows a wearer to tighten upper 102 over his or her foot.

Upper 102 shown in FIG. 1 may include one or more material elements (for example, meshes, textiles, foam, leather, and synthetic leather), which may be joined to define an interior void configured to receive a foot of a wearer. The material elements may be selected and arranged to selectively impart properties such as light weight, durability, air-permeability, wear-resistance, flexibility, and comfort. At least a portion of sole structure 104 may be fixedly attached to upper 102 (for example, with adhesive, stitching, welding, or other suitable techniques) and may have a configuration that extends between upper 102 and the ground. Sole structure 104 may include provisions for attenuating ground reaction forces (that is, cushioning and stabilizing the foot during vertical and horizontal loading). In addition, sole structure 104 may be configured to provide traction, impart stability, and control or limit various foot motions, such as pronation, supination, or other motions.

In some embodiments, sole structure 104 may be configured to provide traction for article of footwear 100. In addition to providing traction, sole structure 104 may attenuate ground reaction forces when compressed between the foot and the ground during walking, running, jumping or other athletic activities. The configuration of sole structure 104 may vary significantly in different embodiments to include a variety of conventional or non-conventional structures. In some cases, sole structure 104 can be configured according to one or more types of ground surfaces on which sole structure 104 may be used.

For example, the disclosed concepts may be applicable to footwear configured for use on any of a variety of surfaces, including indoor surfaces or outdoor surfaces. The configuration of sole structure 104 may vary based on the properties and conditions of the surfaces on which article of footwear 100 is anticipated to be used. For example, sole structure 104 may vary depending on whether the surface is harder or softer. In addition, sole structure 104 may be tailored for use in wet or dry conditions.

In some embodiments, sole structure 104 may be configured for a particularly specialized surface or condition. The proposed footwear upper construction may be applicable to any kind of footwear, such as basketball, soccer, track and football, as well as footwear designed for other athletic activities. Accordingly, in some embodiments, sole structure 104 may be configured to provide traction and stability on hard indoor surfaces (such as hardwood), soft, natural turf surfaces, or on hard, artificial turf surfaces. In some embodiments, sole structure 104 may be configured for use on multiple different surfaces. In addition, in some cases, sole structure 104 can include one or more cleat members or traction elements that are configured to increase traction with a ground surface.

In some embodiments, sole structure 104 may include multiple components, which may individually or collectively provide article of footwear 100 with a number of attributes, such as support, rigidity, flexibility, stability, cushioning, comfort, reduced weight, or other attributes. In some embodiments, sole structure 104 may include an insole/sockliner, a midsole, and a ground-contacting outer sole member or outsole, which may have an exposed, ground-contacting lower surface. In some cases, however, one or more of these components may be omitted.

Embodiments of article of footwear 100 may include a tensioning apparatus 200. Tensioning apparatus 200 may comprise various components and systems, such as, for example, an electric motor, for fastening upper 102 over a wearer's foot. In some embodiments, tensioning apparatus 200 may include laces and/or cables that can be tensioned to close upper 102 over a wearer's foot.

A lace as used with article of footwear 100 may comprise any type of lacing material known in the art. Examples of laces that may be used include cables or fibers having a low modulus of elasticity as well as a high tensile strength. A lace may comprise a single strand of material, or can comprise multiple strands of material. An exemplary material for the lace is SPECTRA™, manufactured by Honeywell of Morris Township N.J., although other kinds of extended chain, high modulus polyethylene fiber materials can also be used as a lace.

In some embodiments, tensioning apparatus 200 may use an input assembly 300 to control tensioning apparatus 200. FIGS. 1-6 illustrate an embodiment of an input assembly 300 for a tensioning apparatus 200 in the context of an article of footwear 100. Input assembly 300 in some cases may include one or more input devices, such as one button or multiple buttons, one sensor or multiple sensors, and/or one or more passive or active devices that respond to internal or external stimuli. Input assembly 300 may also include a combination of such input devices.

FIG. 1 and FIG. 2 are schematic diagrams showing an embodiment of an input assembly for controlling a tensioning apparatus. This embodiment is shown in the context of an article of footwear 100. Sole 104 may have a midsole 151. Upper 102 has a lacing system 150 that is mechanically connected to tensioning apparatus 200 (shown schematically in FIG. 2). Lace guides 156 on the lateral side 107 and the medial 106 side of upper 102 route laces and/or cables down to the sole, where they are connected to tensioning apparatus 200. Tensioning apparatus 200 may be controlled by input assembly 300 and may receive power from battery 231. Under the control of input assembly 300, tensioning apparatus 200 can tighten or loosen the laces to close or open upper 102 over a wearer's foot.

For example, in the embodiment shown in FIGS. 1-6, input assembly 300 has a first button 321 and a second button 322 that function as the input devices. First button 321 and second button 322 are mounted on a printed circuit board 320. In some embodiments, printed circuit board 320 may be a flexible printed circuit board. In other embodiments, printed circuit board 320 may be a rigid printed circuit board. Input assembly 300 further includes a first pair of wires 302 and a second pair of wires 304. First pair of wires 302 and second pair of wires 304 are electrically connected to printed circuit board 320 at a wires-to-circuit board connection that includes a first connection point 311, a second connection point 312, a third connection point 313 and a fourth connection point 314, as described below with reference to FIG. 7. First pair of wires 302 and second pair of wires 304 may be used to electrically activate tensioning apparatus 200 under the control of first button 321 or second button 322.

As shown in FIGS. 1-2, tensioning apparatus 200 may be controlled via an input assembly 300. In this embodiment, input assembly 300 may be disposed on the lateral side 107 of upper 102, on the heel portion of upper 102. In other embodiments, input assembly 300 may be disposed on the medial side 106 of upper 102, at the back of the heel of upper 102 or elsewhere on upper 102, or may be disposed in sole 104.

When a wearer of article of footwear 100 is walking, running, jumping or otherwise exercising, the material of upper 102 may flex, stretch, wrinkle, and/or bend. Such actions may apply tensioning stress and/or flexing stress to input assembly 300, most acutely at the wires-to-circuit board connection, for example at first connection point 311, second connection point 312, third connection point 313 and/or fourth connection point 314, possibly leading to failure of the tensioning apparatus. Embodiments of the input assembly 300, such as the input assembly illustrated in FIGS. 1-6, include provisions for relieving tension and stress at these connection points and elsewhere in the tensioning apparatus, as described below with reference to FIGS. 3-7.

Input assembly 300 is shown in isolation in FIGS. 3-6. As noted above, in this embodiment, input assembly 300 may include, for example, a printed circuit board 320 including a first button 321 and a second button 322. Each of first button 321 and second button 322 may be surrounded by a protective ring 420. In this embodiment first button 321 and second button 322 may be electrically connected to tensioning apparatus 200 via a first pair of wires 302 and a second pair of wires 304. First pair of wires 302 includes a first wire 305 and a second wire 306. Second pair of wires 304 includes a third wire 307 and a fourth wire 308. Power from battery 231 may be applied to tensioning apparatus 200 as directed by first button 321 or by second button 322.

Some embodiments can include provisions that can accommodate relative motion or tension between proximal end 341 and distal end 342. In some embodiments, the first pair of wires 302 and/or the second pair of wires 304 are arranged in a particular manner to accommodate this relative motion or tension between proximal end 341 and distal end 342. As shown in FIG. 2, and in more detail in FIGS. 3-6, first pair of wires 302 has a first twisted loop 351 disposed between its proximal end 341 and its distal end 342. Likewise, second pair of wires 304 has a second twisted loop 361 disposed between its proximal end 343 and its distal end 344. Referring to FIGS. 3-6, in one embodiment twisted loop 351 in the first pair of wires 302 may be formed by a first inner retaining member 352. Inner retaining member 352 allows first pair of wires 302 to slide through inner retaining member 352, thus allowing the length of first pair of wires 302 outside of first twisted loop 351 to increase or decrease. Optionally, first twisted loop 351 may also have a first outer retaining member 353, fixedly holding first wire 305 and second wire 306 together at an outer portion of first twisted loop 351. As described below with respect to FIGS. 3-6, first twisted loop 351 and second twisted loop 361 function to relieve any tension along first pair of wires 302 and second pair of wires 304, as the wearer of the article of footwear engages in athletic activity, or as the upper is being tightened.

In this embodiment, second twisted loop 361 in second pair of wires 304 may be formed by a second inner retaining member 362 as shown in FIGS. 3-6. Second inner retaining member 362 allows second pair of wires 304 to slide through second inner retaining member 362, thus allowing the length of second pair of wires 304 outside of second twisted loop 361 to increase or decrease. Optionally, second twisted loop 361 may also have a second outer retaining member 363, fixedly holding third wire 307 and fourth wire 308 together at an outer portion of second twisted loop 361. For example, first pair of wires 302 may slide through inner retaining member 352 and second pair of wires 304 may slide through inner retaining member 362 as the wearer of the footwear is walking, running jumping, or leaping.

Figure 3:
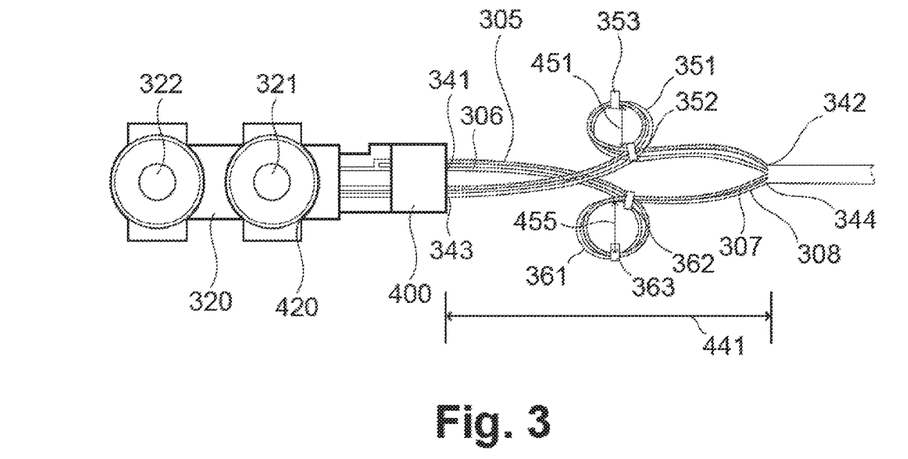
FIG. 3 is a schematic diagram of an embodiment of an input assembly that is not under tension.

FIG. 3 shows input assembly 300 in its initial condition, for example just after the article of footwear has been manufactured. In that initial condition, the input assembly might be under some level of tension, or might experience no tension. FIG. 3 may also represent the configuration of input assembly 300 when the article of footwear is not being worn, or possibly when the wearer is relaxing on a bench with his or her upper fully loosened. In this initial state, the distance between the proximal end 341 of first pair of wires 302 and the distal end 342 of first pair of wires 302 is shown as length 441. In many cases, the distance between the proximal end 343 of the second pair of wires 304 to the distal end 344 of the second pair of wires 304 may also be roughly about length 441.

Figure 4:
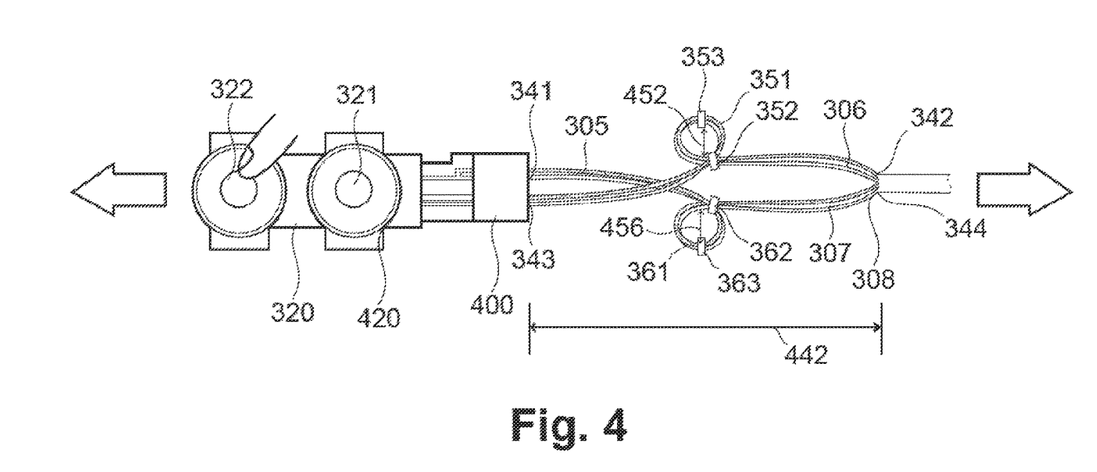
FIG. 4 is a schematic diagram of an embodiment of an input assembly as the upper of the article of footwear is being tightened.
Figure 5:
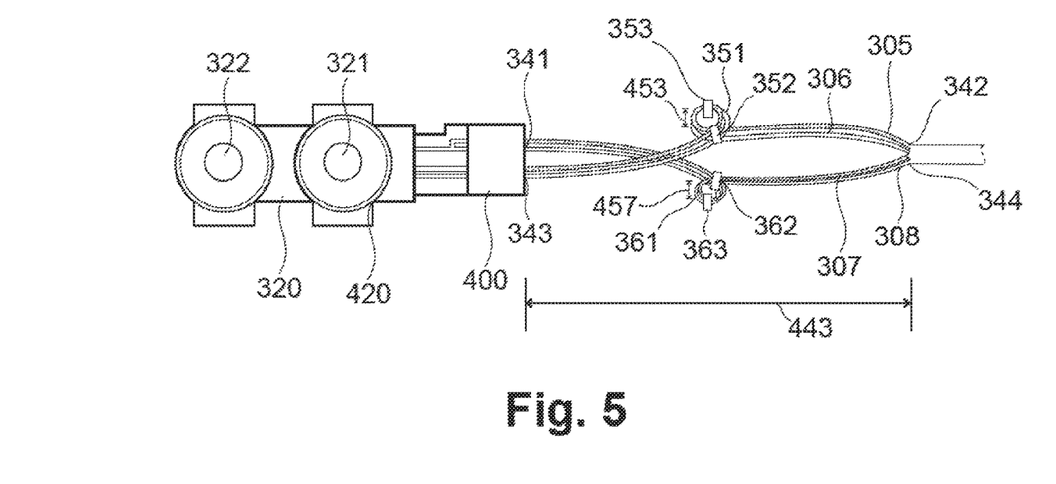
FIG. 5 is a schematic diagram of an embodiment of an input assembly when the article of footwear has been fully tightened.

FIG. 4 shows input assembly 300 as the wiring experiences tension. The wiring may experience tension for any number of reasons, for example when the wearer is walking or running, or when the article of footwear is being pulled onto the wearer's foot, or when second button 322 is being depressed, activating tensioning apparatus 200 to tighten the upper. In this case, the distance between the proximal end 341 and the distal end 342 of first pair of wires 302 has increased to length 442, where length 442 is greater than length 441. In this tightened configuration, the diameter 452 of first twisted loop 351 and the diameter 456 of second twisted loop 361 generally decrease. Thus, the diameter 452 of first twisted loop 351 in FIG. 4 may be smaller than the diameter of first twisted loop 451 in FIG. 3, and the diameter 456 of second twisted loop 361 may be smaller than the diameter 455 of second twisted loop 361 in FIG. 3. In many cases, the distance between the proximal end 343 of the second pair of wires 304 to the distal end 344 of second pair of wires 304 may also be roughly about length 442, FIG. 5 shows input assembly 300 after the upper has experienced even greater tension. This may happen, for example, when the wearer is jumping, lunging or pivoting, or when the upper has been fully tightened over the wearer's foot. In this case, the distance between the proximal end 341 of first pair of wires 302 and the distal end 342 of first pair of wires 302 has increased to length 443, where length 443 is greater than length 442. In this configuration, the diameter 453 of first twisted loop 351 may be smaller than the diameter 452 of first twisted loop 351 in FIG. 4, and the diameter 457 of second twisted loop 361 in FIG. 5 may be smaller than the diameter 455 of second twisted loop 361 in FIG. 4. In some cases, the distance between the proximal end 343 of the second pair of wires 304 to the distal end 344 of second pair of wires 304 may also roughly be about length 443.

Figure 6:
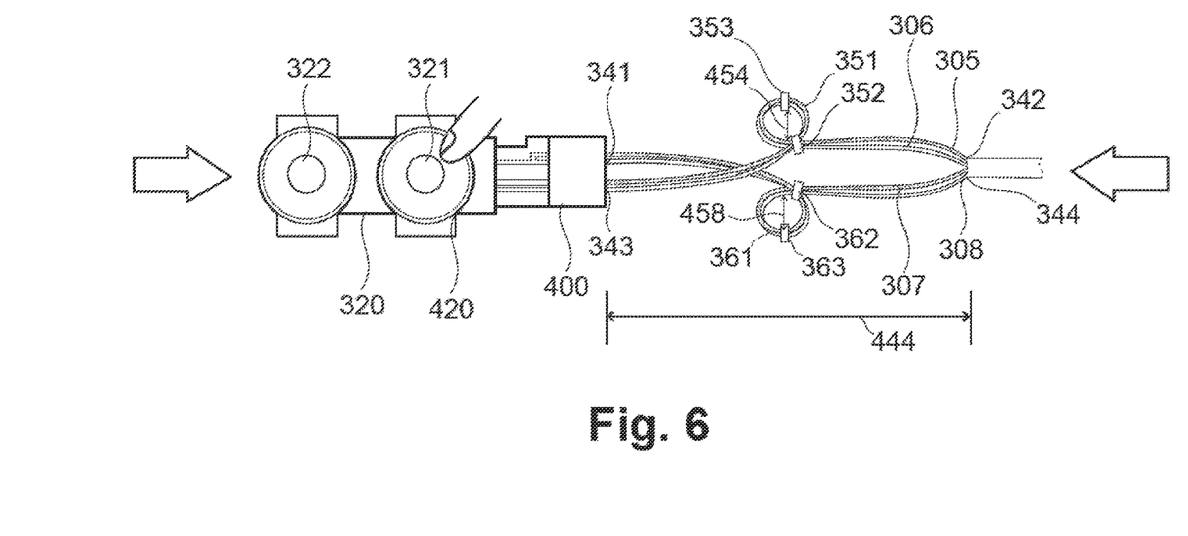
FIG. 6 is a schematic diagram of an embodiment of an input assembly as the upper of the article of footwear is being loosened.

FIG. 6 shows input assembly 300 as it returns to a reduced tension state. This may happen when the source of the added tension is removed or reduced. For example, this may occur when the wearer is resting on the bench, or when the wearer's foot is in the air during a jump, or when the first button 321 is being depressed, activating tensioning apparatus 200 to loosen upper 102 over the wearer's foot. In this case, the distance between the proximal end 341 of first pair of wires 302 and the distal end 342 of first pair of wires 302 has decreased to length 444, where length 444 is less than length 443. In this intermediate configuration, the diameter 454 of first twisted loop 351 in FIG. 6 may be greater than the diameter 453 of first twisted loop 351 in FIG. 5, and the diameter 458 of second twisted loop 361 may be greater than the diameter 457 of second twisted loop 361 in FIG. 5. In many cases, the distance between the proximal end of the second pair of wires 304 to the distal end of second pair of wires 304 may also be roughly about length 444, but n other cases that distance may have another value.

FIGS. 3-6 also show an embodiment of flexible epoxy cover 400. Although flexible epoxy cover 400 is flexible, such that it may curve so as to accommodate first pair of wires 302 and second pair of wires 304 as they approach printed circuit board 320 at an angle, flexible epoxy cover has limited flexibility. Essentially, flexible epoxy cover 400 has an intermediate flexibility: it is more flexible than printed circuit board 320, but less flexible than first pair of wires 302 or second pair of wires 304. Because flexible epoxy cover 400 has only limited flexibility, flexible epoxy cover 400 allows only a limited degree of flexion or bending between the first pair of wires 302 and the second pair of wires 304 on the one hand, and printed circuit board 320 on the other, as will be discussed below with respect to FIGS. 7-10. In other words, flexible epoxy cover curves rather than bending sharply, which limits the connecting angles of the wires at the connection points, as described below with respect to FIGS. 7-10. In this way, flexible epoxy cover 400 protects first connection point 311, second connection point 312, third connection point 313 and fourth connection point 314 on printed circuit board 320.

This structure allows some limited flexion between the wires and the printed circuit board to accommodate relative motion between the wires and the printed circuit board, but reduces fatigue at the connection points due to cyclic bending, that might otherwise lead to failure of one or more of the connections. In general, the selection of the material for the flexible epoxy cover may be based upon criteria such as the flexibility and size of the printed circuit board, the flexibility and dimensions of the wires and/or the nature of the connections from the wires to the printed circuit board. In some cases, the degree of flexibility of the flexible epoxy covers may be defined by their durometer hardness. For example, in some embodiments, flexible epoxy cover may have a durometer hardness between 20 and 40 on the Shore D scale, such as a durometer hardness of 30. In other embodiments, flexible epoxy cover 400 may have a durometer hardness in the range of 20 to 40 on the Shore A scale, for example a durometer hardness of about 30 on the Shore A scale.

Figure 7:
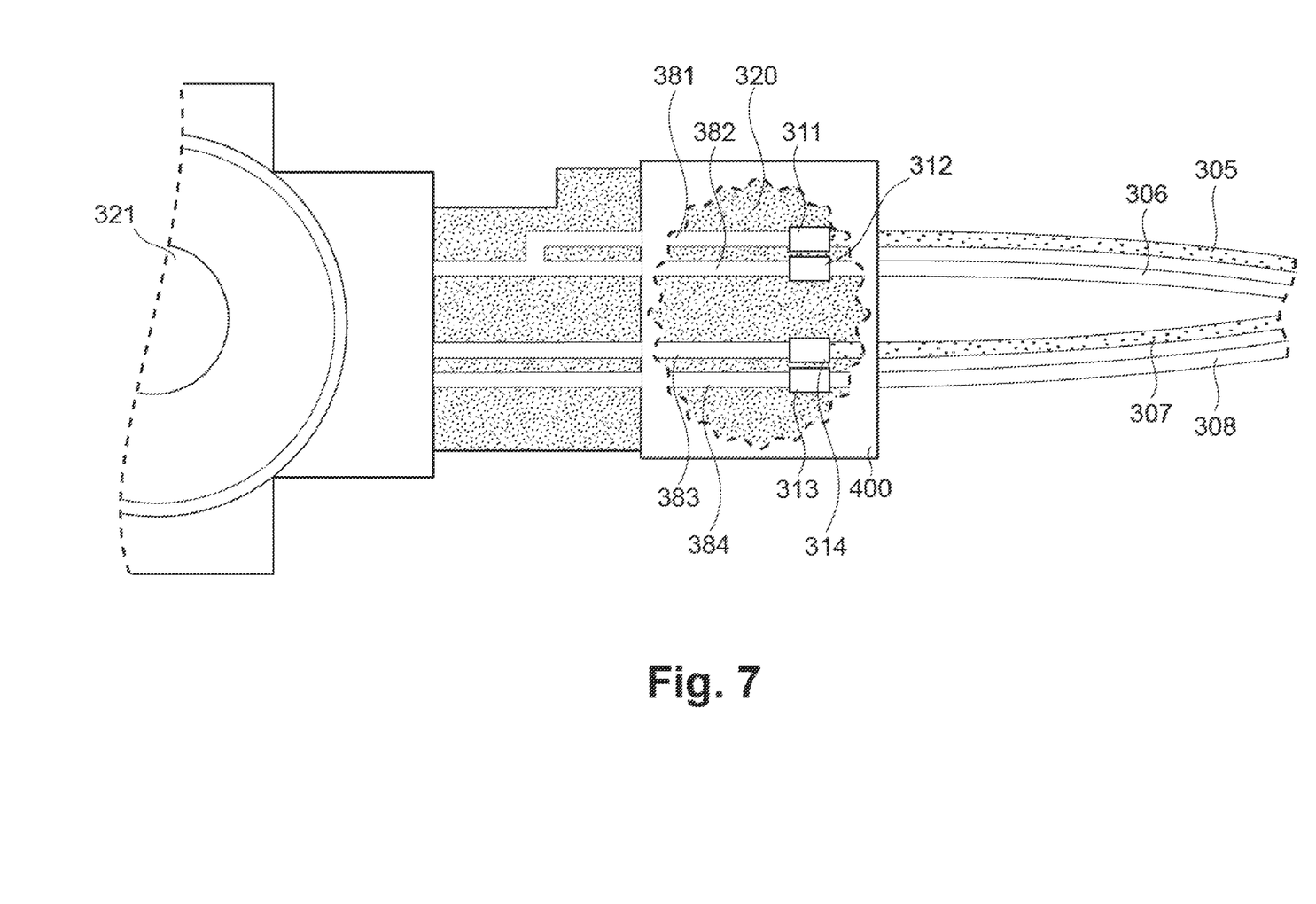
FIG. 7 is a schematic diagram of an embodiment of the connections of wires to the printed circuit board.

FIG. 7 is a cutaway view showing internal portions of the embodiment of an input assembly shown in FIGS. 3-6. The cutaway portion of this figure shows an embodiment of wires as they are connected with their respective connection points. The connection points may be plug-and-jack connections, soldering connections, welding connections, mechanical connections or any other kind of connection that provides electrical contact from the printed circuit board to the wires. FIG. 7 shows the connection of first wire 305 to first printed conductor 381 at first connection point 311, the connection of second wire 306 to second printed conductor 382 at second connection point 312, the connection of third wire 307 to third printed conductor 383 at third connection point 313 and the connection of fourth wire 308 to fourth printed conductor 284 at fourth connection point 314. Wire 305, wire 306, wire 307 and wire 308 are not visible on the printed circuit board outside of the cutaway region, because they are covered by epoxy cover 400. For the same reason, conductor 381, conductor 382, conductor 383 and conductor 384 are not visible under the epoxy cover 400 outside of the cutaway region, although they are shown on the printed circuit board to the left of the epoxy cover.

Figure 8:
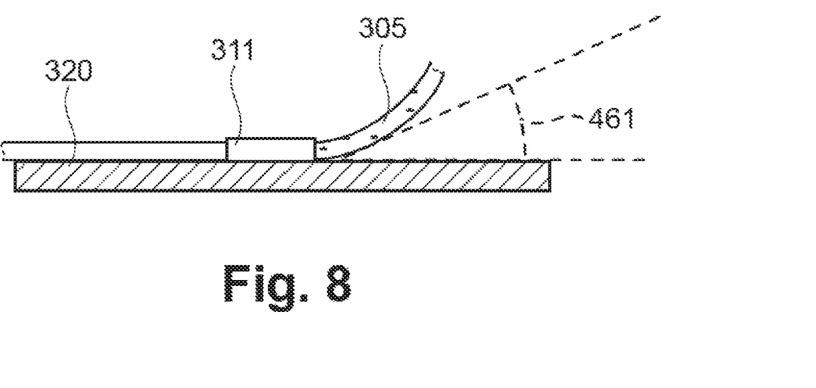
FIG. 8 is a side cross-sectional view of an embodiment of a wire connected to the printed circuit board, showing a vertical connecting angle between a wire and the printed circuit board.
Figure 9:
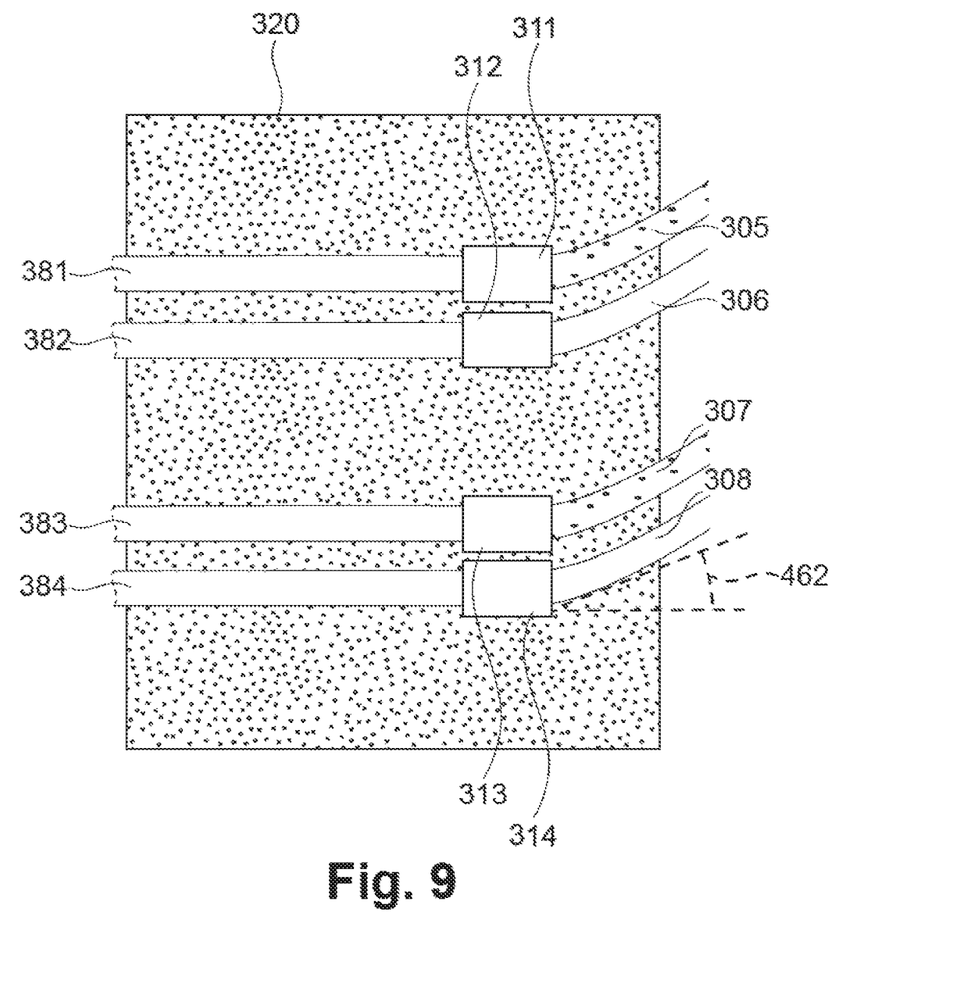
FIG. 9 is a plan view of an embodiment of a wire connected to the printed circuit board, showing of a lateral connecting angle between a wire and a printed conductor on the printed circuit board.

As noted above, flexible epoxy cover 400 prevents any sharp bending of the first pair of wires 302 or of the second pair of wires 304 at the points that they are connected to printed circuit board 320. Basically, because flexible epoxy cover 420 is made of a material that resists sharp bending, the wires can only approach their connecting points along a gentle curve. This may limit the amplitude of the connecting angle between the wires and the printed circuit board to less than 5° or in many cases to less than 2°. For example, if first pair of wires 302 approaches printed circuit board 320 at a vertical connecting angle 461 as shown in FIG. 8, connecting angle 461 may be limited by the epoxy cover to less than about 5° in some cases. In other cases, connecting angle 461 may be limited by the epoxy cover to less than about 2°. Similarly, if the first pair of wires approaches printed circuit board 320 at a horizontal connecting angle 462 as shown in FIG. 9, that connecting angle may also be limited to less than about 5° in some cases, and in some cases to less than 2°.

Figure 10:
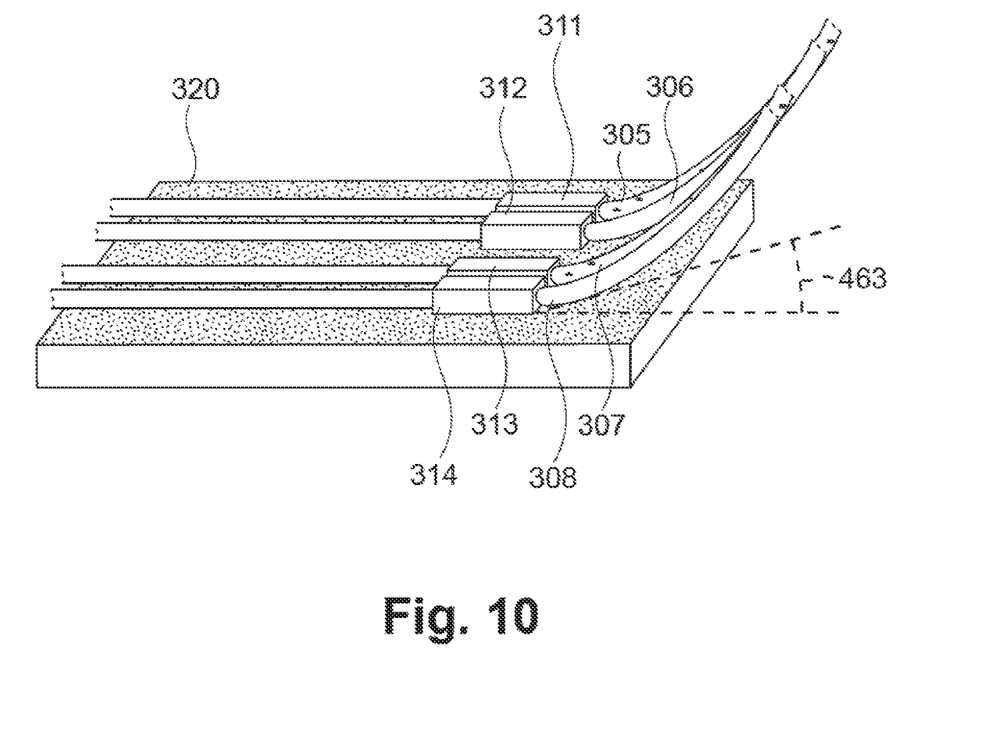
FIG. 10 is a perspective view of an embodiment of wires attached to the printed circuit board, shown with the top epoxy cover removed for clarity, showing an oblique connecting angle between the wires and the printed circuit board.

FIG. 10 is a schematic diagram of a perspective view of an embodiment with the wires attached to the printed circuit board. For clarity, the printed circuit board is shown without its epoxy cover. If the first pair of wires approaches printed circuit board 320 at an oblique connecting angle 463 as shown in FIG. 10, that connecting angle may also be limited to less than 5° and in some cases to less than 2°. It should be noted that the connecting angles shown in FIGS. 8-10 have been exaggerated to make the angles more easily identifiable.

In operation, in the embodiment shown in FIGS. 1-7, tensioning apparatus 200 responds to signals received from input assembly 300 to tighten or loosen the upper over a wearer's foot. In combination, twisted loop 351, twisted loop 361 and flexible epoxy cover 400 function to respond to tension that may be applied to the wiring, as well as to accommodate bending of the upper fabric while the wearer is running, walking, jumping or engaging in any other athletic activity to reduce the stress at the connection points.

Although the embodiment shown in FIG. 1 and FIG. 2 has a battery 231 in the back of the heel of the article of footwear, in other embodiments the battery may be located elsewhere in the heel, the sole or the upper of the article of footwear. In some embodiments, battery 231 may be a rechargeable battery that may be recharged either via external inputs (not shown), or by coupling from a charging device to internal inductive loops disposed in the sole structure, for example. In other embodiments, battery 231 may be a rechargeable battery that may be recharged by amorphous or crystalline photovoltaic cells, by electromechanical devices and/or by piezoelectric devices.

Examples of button assemblies that may be used in the embodiments described herein are described in Tiffany Beers et al., U.S. Patent Publication Number 2017-0265561-A1, published Sep. 21, 2017 (previously U.S. patent application Ser. No. 15/070,162, filed Mar. 15, 2016), titled "A Standoff Unit for a Control Device in an Article of Footwear," which is incorporated herein in its entirety.

In different embodiments, any of the components described herein could be disposed in any other portions of an article, including various regions of the upper and/or sole structure. In some cases, some component parts (such as lead wires, etc.) could be disposed in one portion of an article and other component parts (such as the battery and the tensioning apparatus) could be disposed in another, different, portion. The location of one or more component parts may be selected according to various factors including, but not limited to: size constraints, manufacturing constraints, aesthetic preferences, optimal design and functional placement, ease of removability or accessibility relative to other portions of the article, as well as possibly other factors.

In some cases, the tightening or loosening of an article of footwear 100 can occur in discrete steps so that each time the wearer presses a button, the tensile elements are pulled in or let out by a predetermined amount. In other cases, this incremental loosening or tightening can occur in a continuous manner, as long as the wearer continues to depress the first button 321 to loosen or the second button 322 to tighten the upper over the wearer's foot. In some cases, the speed of tightening can be set so that the system does not overshoot a preferred level of tightness (i.e., the system doesn't move between not tight enough and too tight too quickly) while also being fast enough to avoid overly long times for fully loosening article of footwear 100. With this arrangement, a wearer can continue increasing and decreasing the tension throughout article of footwear 100 (using the incremental tighten and incremental loosen modes) until a preferred level of tightness for upper 102 is achieved.

It should be understood that the embodiments and features described herein are not limited to a particular user interface or application for operating a tensioning apparatus. Furthermore, the embodiments disclosed herein are intended to be exemplary, and other embodiments could incorporate any additional control buttons, interface designs and software applications. The control buttons, sensors or other devices for initiating various operating commands can be selected according to various factors including: ease of use, aesthetic preferences of the designer, software design costs, operating properties of the system, as well as possibly other factors. Furthermore, a variety of products, including apparel (e.g., shirts, pants, footwear) and protective gear or braces (e.g., helmets, knee braces, elbow pads), may incorporate an embodiment of the input assembly described herein.

Furthermore, the embodiments described herein may also include or refer to techniques, concepts, features, elements, methods, and/or components from Tiffany Beers et al., U.S. Patent Publication Number 2016/0345679 A1, published Dec. 1, 2016 (previously U.S. patent application Ser. No. 14/723,972, filed May 28, 2015), titled "An Article of Footwear and a Method of Assembly of the Article of Footwear;" Holli Pheil et al., U.S. Patent Publication Number 2016-0345653, published Dec. 1, 2016, (previously U.S. patent application Ser. No. 14/723,832, filed May 28, 2015), titled "A Lockout Feature for a Control Device;" Tiffany Beers et al., U.S. Patent Publication Number 2016-0345654, published Dec. 1, 2016, (previously U.S. patent application Ser. No. 14/723,880, filed May 28, 2015), titled "A Charging System for an Article of Footwear"; and Tiffany Beers et al., U.S. Patent Publication Number 2016-0345671 A1, published Dec. 1, 2016, now U.S. Pat. No. 9,894,954 which issued on Feb. 20, 2018, (previously U.S. patent application Ser. No. 14/723,994, filed May 28, 2015), titled "A Sole Plate for an Article of Footwear," the entirety of each of the foregoing applications being incorporated hereinby reference.

While various embodiments have been described, the description is intended to be exemplary, rather than limiting and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. An input assembly comprising:
 a first conductor having a proximal end and a distal end;
 a second conductor having a proximal end and a distal end;
 a printed circuit board having a first connection point and a second connection point, the first conductor being connected at the distal end to the first connection point, the second conductor being connected at the distal end to the second connection point;

the first conductor forming a first twisted loop between the distal end of the first conductor and the proximal end of the first conductor, said first twisted loop having a first diameter and the second conductor forming a second twisted loop between the distal end of the second conductor and the proximal end of the second conductor, said second twisted loop having a second diameter, such that the first twisted loop and the second twisted loop form opposed twisted loops;

wherein the first twisted loop includes a first inner retaining member slidably holding the first conductor; and the second twisted loop includes a second inner retaining member slidably holding the second conductor.

2. The input assembly of claim 1, wherein the first twisted loop further includes a first outer retaining member fixedly holding the first conductor, and wherein the second twisted loop further includes a second outer retaining member fixedly holding the second conductor.

3. The input assembly of claim 1, wherein when the distance from the proximal end of the first conductor to the distal end of the first conductor increases, the first diameter decreases and the second diameter decreases.

4. The input assembly of claim 1, wherein when the distance from the proximal end of the first conductor to the distal end of the first conductor decreases, the first diameter increases and the second diameter increases.

5. The input assembly of claim 1, wherein the first twisted loop operates to reduce tension between the distal end of the first conductor and the first connection point and the second twisted loop operates to reduce tension between the distal end of the second conductor and the second connection point when the distance between the proximal end of the first conductor and the distal end of the first conductor increases.

6. The input assembly of claim 1, further comprising a flexible epoxy cover enclosing the first connection point and the distal end of the first conductor and the second connection point and the distal end of the second conductor.

7. The input assembly of claim 6, wherein the distal end of the first conductor and the distal end of the second conductor are connected to the printed circuit board at connecting angles, and wherein the flexible epoxy cover limits the connecting angles to less than 5°.

8. A method, comprising:
forming a first pair of conductors having a proximal end and a distal end, said first pair of conductors comprising a first conductor and a second conductor, wherein the first conductor has a proximal end and a distal end and the second conductor has a proximal end and a distal end;

forming a second pair of conductors having a proximal end and a distal end, said second pair of conductors comprising a third conductor and a fourth conductor, wherein the third conductor has a proximal end and a distal end, and the fourth conductor has a proximal end and a distal end;

obtaining a printed circuit board having a first connection point, a second connection point, a third connection point and a fourth connection point;

connecting the first conductor being connected at the distal end to the first connection point, the second conductor being connected at the distal end to the second connection point, the third conductor being connected at the distal end to the third connection point and the fourth conductor being connected at the distal end to the fourth connection point;

wherein the first pair of conductors forming a first twisted loop between the distal end of the first pair of conductors and the proximal end of the first pair of conductors, said first twisted loop having a first diameter and the second pair of conductors forming a second twisted loop between the distal end of the second pair of conductors and the proximal end of the second pair of conductors, said second twisted loop having a second diameter, such that the first twisted loop and the second twisted loop form opposed twisted loops;

securing a first inner retaining member slidably holding both the first conductor and the second conductor; and securing a second inner retaining member slidably holding both the third conductor and the fourth conductor.

9. The method of claim 8, further comprising:
securing a first outer retaining member fixedly holding both the first conductor and the second conductor; and securing a second outer retaining member fixedly holding both the third conductor and the fourth conductor.

10. The method of claim 8, wherein when the distance from the proximal end of the first pair of conductors to the distal end of the first pair of conductors increases, the first diameter decreases and the second diameter decreases.

11. The method of claim 8, wherein when the distance from the proximal end of the first pair of conductors to the distal end of the first pair of conductors decreases, the first diameter increases and the second diameter increases.

12. The method of claim 8, wherein the first twisted loop operates to reduce tension between the distal end of the first conductor and the first connection point and the second twisted loop operates to reduce tension between the distal end of the third conductor and the third connection point when the distance between the proximal end of the first pair of conductors and the distal end of the first pair of conductors increases.

13. The method of claim 8, further comprising enclosing, with a flexible epoxy cover, the first connection point and the distal end of the first conductor, the second connection point and the distal end of the second conductor, the third connection point and the distal end of the third conductor, and the fourth connection point and the distal end of the fourth conductor.

14. The method of claim 13, wherein the distal end of the first conductor, the distal end of the second conductor, the distal end of the third conductor and the distal end of the fourth conductor are connected to the printed circuit board at connecting angles, and wherein the flexible epoxy cover limits the connecting angles to less than 5°.

15. An input assembly comprising:
a first pair of conductors having a proximal end and a distal end, said first pair of conductors comprising a first conductor and a second conductor, wherein the first conductor has a proximal end and a distal end and the second conductor has a proximal end and a distal end;

a second pair of conductors having a proximal end and a distal end, said second pair of conductors comprising a third conductor and a fourth conductor, wherein the third conductor has a proximal end and a distal end, and the fourth conductor has a proximal end and a distal end;

a printed circuit board having a first connection point, a second connection point, a third connection point and a fourth connection point;

the first conductor being connected at the distal end to the first connection point, the second conductor being connected at the distal end to the second connection point, the third conductor being connected at the distal end to the third connection point and the fourth conductor being connected at the distal end to the fourth connection point;

the first pair of conductors forming a first twisted loop between the distal end of the first pair of conductors and the proximal end of the first pair of conductors, said first twisted loop having a first diameter and the second pair of conductors forming a second twisted loop between the distal end of the second pair of conductors and the proximal end of the second pair of conductors, said second twisted loop having a second diameter;

the first twisted loop includes a first inner retaining member slidably holding both the first conductor and the second conductor; and the second twisted loop includes a second inner retaining member slidably holding both the third conductor and the fourth conductor.

16. The input assembly of claim 15, wherein the first twisted loop further includes a first outer retaining member fixedly holding both the first conductor and the second conductor, and wherein the second twisted loop further includes a second outer retaining member fixedly holding both the third conductor and the fourth conductor.

17. The input assembly of claim 15, wherein when the distance from the proximal end of the first pair of conductors to the distal end of the first pair of conductors increases, the first diameter decreases and the second diameter decreases.

18. The input assembly of claim 15, wherein when the distance from the proximal end of the first pair of conductors to the distal end of the first pair of conductors decreases, the first diameter increases and the second diameter increases.

19. The input assembly of claim 15, wherein the first twisted loop operates to reduce tension between the distal end of the first conductor and the first connection point and the second twisted loop operates to reduce tension between the distal end of the third conductor and the third connection point when the distance between the proximal end of the first pair of conductors and the distal end of the first pair of conductors increases.

20. The input assembly of claim 15, further comprising a flexible epoxy cover enclosing the first connection point and the distal end of the first conductor, the second connection point and the distal end of the second conductor, the third connection point and the distal end of the third conductor, and the fourth connection point and the distal end of the fourth conductor.

* * * * *